United States Patent [19]

Wilhelm

[11] Patent Number: 5,319,543
[45] Date of Patent: Jun. 7, 1994

[54] WORKFLOW SERVER FOR MEDICAL RECORDS IMAGING AND TRACKING SYSTEM

[75] Inventor: Richard K. Wilhelm, Chicago, Ill.

[73] Assignee: First Data Health Services Corporation, Charlotte, N.C.

[21] Appl. No.: 901,362

[22] Filed: Jun. 19, 1992

[51] Int. Cl.$^5$ .............................................. G06F 15/22
[52] U.S. Cl. ................................. 364/401; 364/413.02
[58] Field of Search ............... 364/401, 413.02, 413.13, 364/284, 284.3

[56] References Cited

U.S. PATENT DOCUMENTS

| | | | |
|---|---|---|---|
| 4,958,283 | 9/1990 | Tawara et al. | 364/413.13 |
| 5,101,476 | 3/1992 | Kukla | 364/413.03 |
| 5,168,444 | 12/1992 | Cukor et al. | 364/401 |

*Primary Examiner*—Roy N. Envall, Jr.
*Assistant Examiner*—Frantzy Poinvil
*Attorney, Agent, or Firm*—Pennie & Edmonds

[57] ABSTRACT

A computer system with a workflow server provides for automatic and prioritized assignment of work involving processing of medical information records, or "charts", to particular resources (personnel) in a hospital. In particular, as the system stores data regarding additional medical information records in a relational database, the workflow server identifies which such additional records constitute a new encounter for a particular patient. For each encounter, the system defines one or more visit cases, and may identify for each visit further subset cases for one or more of a number of application programs. Such application programs may include coding/abstracting of documents and assigning deficiencies in documents for completion. The system defines states corresponding to each application program. In response to requests from the application programs, the workflow server routes each defined case to a particular workqueue within the proper state, and then can assign each case to a particular resource (employee) within the proper workqueue. The criteria for the type and number of workqueues within each state, and the criteria for the assignment of resources within each workqueue, can be identified with whatever sophistication or prioritization that a hospital may desire.

12 Claims, 9 Drawing Sheets

WORKFLOW SERVER FOR MEDICAL RECORDS IMAGING AND TRACKING SYSTEM

BACKGROUND OF THE INVENTION

Maintaining patient medical records, whether for an individual doctor or for the entire medical staff of a major hospital, presents many complications, which may be grouped broadly into three categories.

First, pertinent information for any one patient may come from an array of sources, including physical and medical history information provided by the patient, radiology reports, clinical and anatomical pathology reports, EKG readouts, physician orders, nursing notes, care plans, and insurance providers.

Second, upon discharge, a patient's medical record data is typically reviewed extensively. This includes reviews of the physician's attestation, of documentation of the treatment process, of all charts to ensure that they are complete, and of procedures and notes to be abstracted. If data is incomplete, payment organizations such as insurers may deny claims made by a health care provider.

Third, any number of parties require access to patient information, including hospitals, clinics, attorneys, regulatory agencies, courts, whoever pays the bills, and naturally the patients themselves. Keeping track of requests for access from these varied sources is quite burdensome.

Most medical record systems in use today are either paper-based or make use of computer systems only to a limited extent. Optical imaging systems have been used to scan printed documents into a computer system for storage, retrieval, viewing, and printing, but these systems do not provide the management functions needed to deal effectively with the myriad tasks described above. Health care providers are finding that existing systems and methods of managing medical records are not meeting demands placed upon them.

In particular, two administrative bottlenecks in the use of such systems are the coding/abstracting of medical records and the assigning of deficient medical records (e.g., missing data or signatures) to proper personnel for completion.

Existing systems typically store documents in a database on a file server to which a plurality of client workstations are attached. Standard database functions may be used in such systems to establish workflow assignments. But such a database-centered approach to workflow has disadvantages. Because databases are not specifically structured to accommodate the types of transactions required for workflow processing, using standard database functions to carry out such transactions would be inefficient, resulting in unacceptable system performance. This is especially so if sophisticated workflow processing functions are implemented, such as a prioritized assignment of work to particular personnel based on predetermined criteria to specify which employees will receive particular types of work.

A system that allows sophisticated workflow processing while maintaining acceptable system performance would be useful. In addition, in view of the present use of optical imaging technology for data input to the records system, it would be desirable to use such technology in a more automatic system.

SUMMARY OF THE INVENTION

The present invention provides a system that utilizes an application approach to workflow processing. The system includes a number of application programs. One of the application programs is a workflow server that runs as a background procedure on the file server to control the routing of work between application program tasks and individual resources accessing the system via client workstations. The workflow server services requests from other application programs within the system. This eliminates the inefficiencies that result from a database-centered approach to workflow processing, and allows for sophisticated levels of workflow processing.

In particular, as the system stores data regarding additional medical information records (typically documents) in a relational database, it identifies which such additional records constitute a new encounter (i.e., an inpatient or outpatient admission) for a particular patient. An encounter comprises one or more visits by a patient. The system next defines one or more first subsets of records, called visit cases, for each encounter. For each visit case, the system may define second subsets of records for one or more of a number of application programs.

The different application programs correspond to different states within the system. Such states may include coding/abstracting of documents and assigning deficiencies in documents for completion. Preferably, the coding/abstracting application program processes each visit case, while the assign deficiency application program defines deficiency cases as subsets of each visit case for processing by the assign deficiency application. In response to requests from other application programs, the workflow server then routes each defined case to a particular workqueue within the proper application program state. A workqueue is an ordered collection of record subsets (cases) within a state, the contents of which is determined by selection criteria stored in the system. If desired by a user, a workqueue administration application program assigns each case to a particular resource (e.g., a hospital employee) within each workqueue.

The selection criteria for the type and number of workqueues within each state and the selection criteria for the assignment of resources within each workqueue are identified with whatever sophistication or prioritization that a hospital may desire. Specifically, the selection criteria are specified as parameters in a configuration file that is processed when the system is started (i.e., at "run time"). The parameters in the configuration file implement a "code as data" approach: the parameters constitute data that indicate which of a number of segments of program code the system should execute when processing that case. Other parameters may be set in the configuration file, for example, to allow for parallel routing of cases, and for synchronous or asynchronous routing of cases.

The selection criteria parameters in the configuration file may be varied by system administrators before starting the system, (for example, at the beginning of each day) in order to vary the configuration of the workqueues. Thus, the workqueues are said to be configurable at run time.

The workflow server also performs an initial load of the database into memory in order to route cases defined by the system to the appropriate workqueues within the appropriate states and sort the cases within the workqueues. A data-consistent image of the database is thus maintained in memory. Any modifications to the data are written to the database as stored within the system.

The system of the present invention is preferably adapted to run on a client/server system such as Hewlett-Packard's Advanced Image Management System, with client workstations using an operating environment such as Microsoft Windows ®.

A medical records imaging nd tracking system incorporating a workflow server according to the present invention can reduce the storage space needed by hospitals for medical records, reduce backlogs in concluding such tasks as coding/abstracting and completing chart deficiencies by providing multiple user access to the same documents (which may be required for both tasks), increase a hospital's cash flow by reducing the DNFB (discharged, not final billed) period for patients, and improving medical record keeping operations by improving the accuracy of coding/abstracting and standardizing the chart completion process.

BRIEF DESCRIPTION OF THE DRAWINGS

These and other objects, features and advantages of the present invention will be more readily apparent from the following detailed description of the invention in which.

DETAILED DESCRIPTION OF THE PREFERRED EMBODIMENTS

Figure 1:
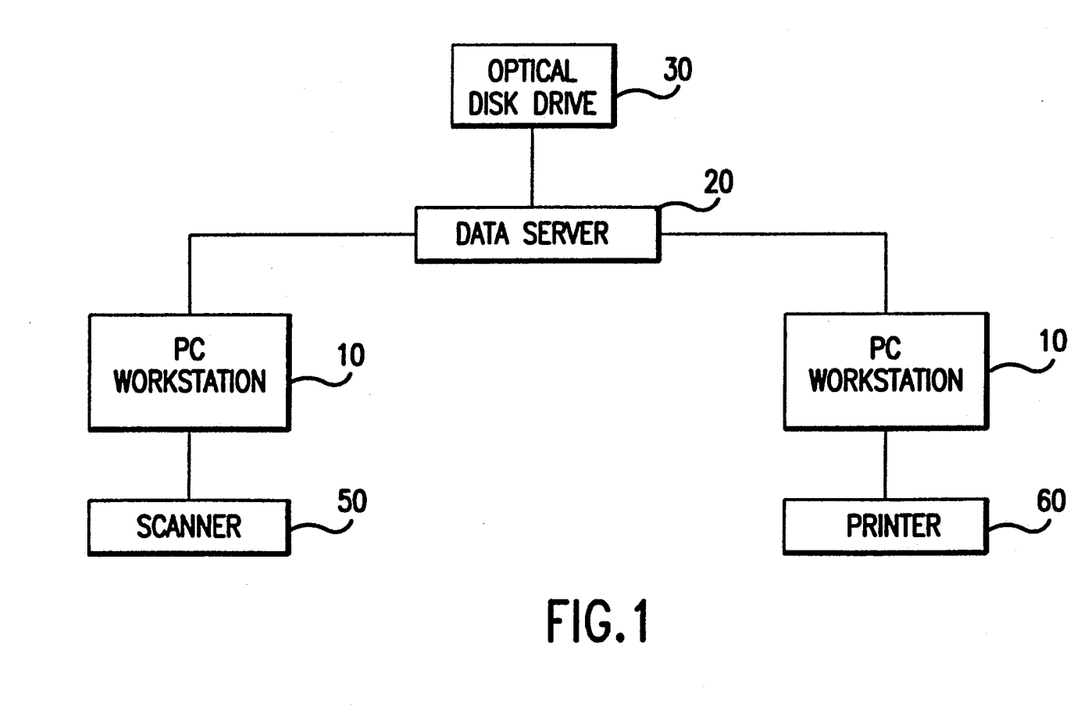
FIG. 1 is a block diagram showing a hardware configuration according to one embodiment of the present invention.

FIG. 1 shows one possible hardware configuration for a system according to the present invention. PC workstations 10 are attached to data server 20, which is attached to optical disk drive 30. Data server 20 passes information stored on optical disk drive 30 to the proper PC workstation 10. An optical scanner 50 (which may include a bar code reading capability) is attached to one PC workstation 10, and a printer 60 is attached to the other PC workstation 10. For this configuration, one PC workstation 10 might be at a nurse's desk, while the other PC workstation 10 might be in a doctor's office.

Figure 2:
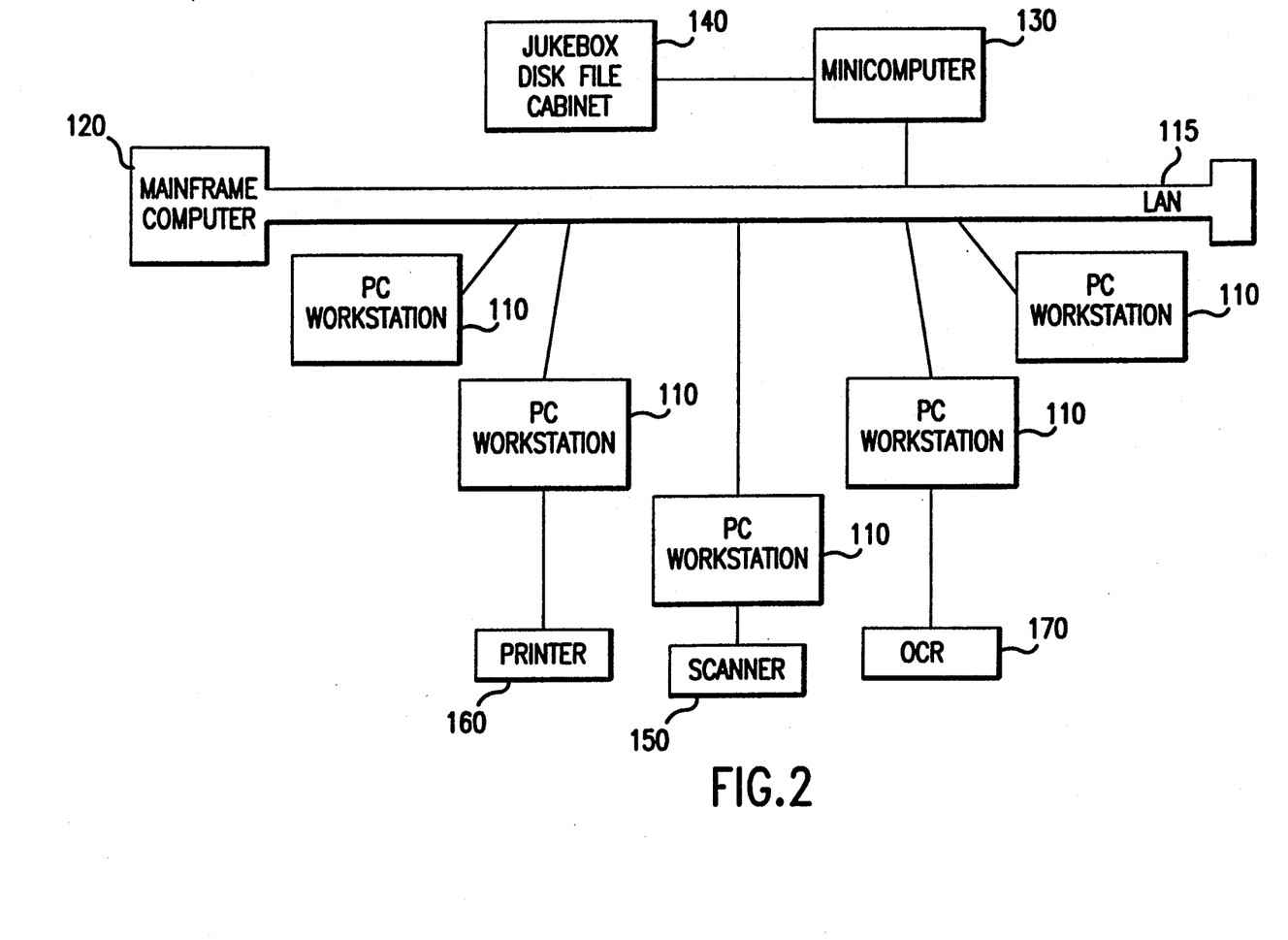
FIG. 2 is a block diagram showing a hardware configuration according to another embodiment of the present invention.

FIG. 2 shows another possible hardware configuration. PC workstations 110 are attached to mainframe computer 120 via local area network (LAN) 115. Minicomputer 130 is also attached to mainframe computer 120 via LAN 115, and jukebox disk file cabinet 140 is attached to minicomputer 130. Each of PC workstations 110 may have direct access to data on mainframe computer 120, or indirect access to data on jukebox disk file cabinet 140 via minicomputer 130. Optical scanner 150 (which preferably includes a bar code reading capability), printer 160, and optical character reader (OCR) 170 may each be attached to one of PC workstations 110. This configuration might be used for an entire small hospital or a single department in a large hospital. Those of skill in the art will recognize that numerous other hardware configurations for the system of the present invention are possible.

Figure 3:
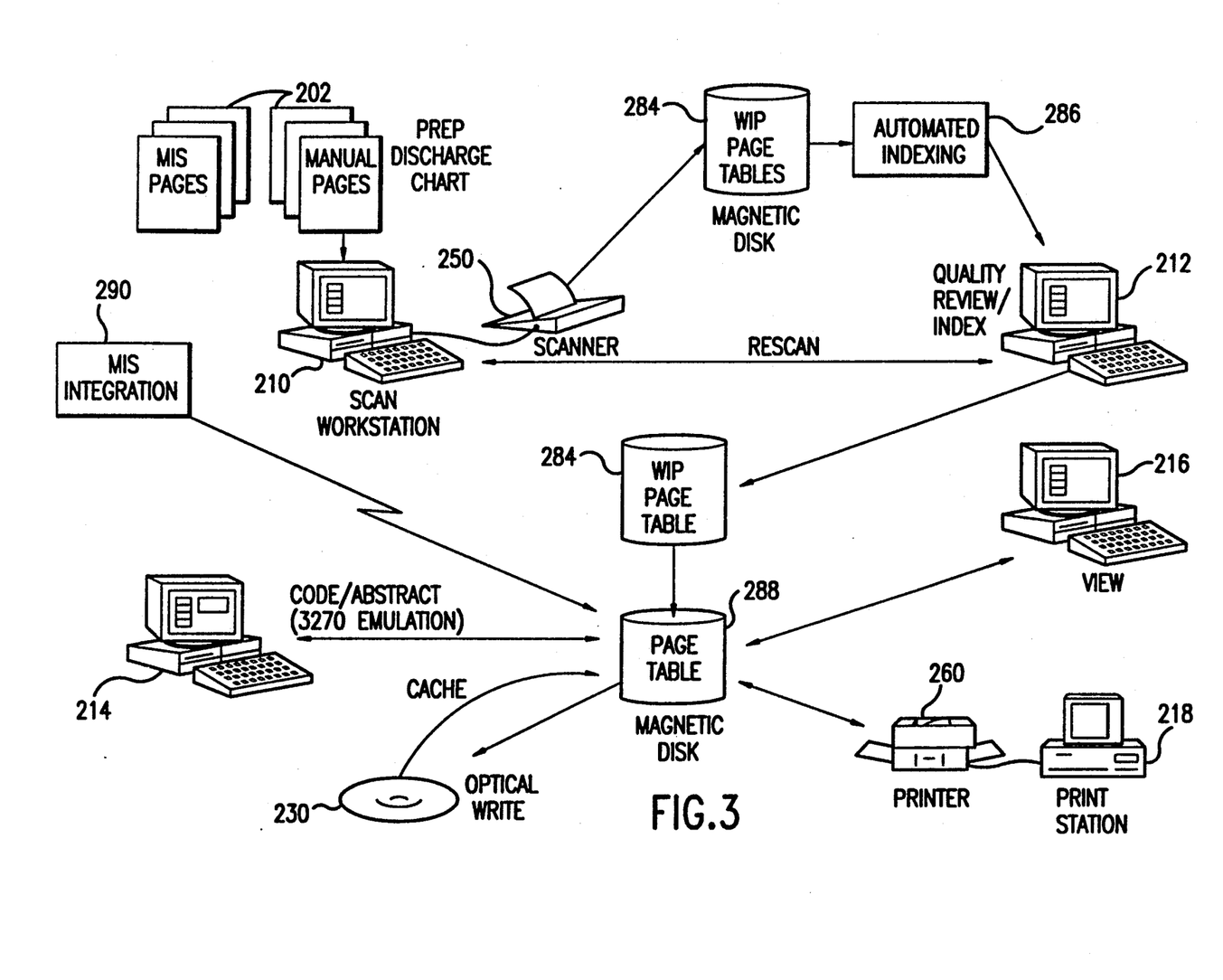
FIG. 3 is a schematic diagram depicting aspects of the implementation of a workflow server according to the present invention in a system such as that of FIGS. 1 or 2.

FIG. 3 is a schematic diagram showing aspects of a system incorporating a workflow server according to the present invention. Scan workstation 210 processes medical record documents 202 received via scanner 250 (which may include a bar code reading capability). Identifying data regarding each document received is stored by scan workstation 210 in a work-in-progress (WIP) page table 284 maintained on a magnetic disk by a file server (not shown). Such identifying data (including document identification (ID) number, document type, and page number) may be included in a bar code placed on each document before scanning. Data in the WIP page table 284 is processed by an automated indexing program 286 running on the file server, which allows for searching and sorting operations on documents received.

Documents that have been scanned may be reviewed at quality review/index workstation 212. Here, an operator may examine the image quality of scanned documents and determine if rescanning of any documents is necessary. In addition, if automated indexing at block 286 was unsuccessful for any document (e.g., a document contained no bar code), the operator may perform the indexing for that document. Information is updated as necessary in WIP page table 284, and then is transferred by the file server to page table 288, a relational database that contains data regarding all medical records, which is also maintained on a magnetic disk. When medical record data is no longer needed for speedy access, it may be written by the file server onto optical disk 230. A cache may be employed when the file server wishes to retrieve information stored on optical disk 230.

Page table 288 may also receive data on medical record documents via MIS integration as indicated at block 290. This process, performed via the file server, allows the entry of documents and other data from other computer systems. One example of MIS integration would be to provide a direct interface to a hospital's computerized admission registration system.

Documents may be accessed via the file server at coding/abstracting workstation 214, or view workstation 216. A plurality of such workstations may be attached to the file server to perform such functions as chart coding/abstracting and chart deficiency completion. Documents may also be accessed at print station 218 and printed on printer 260.

Figure 4:
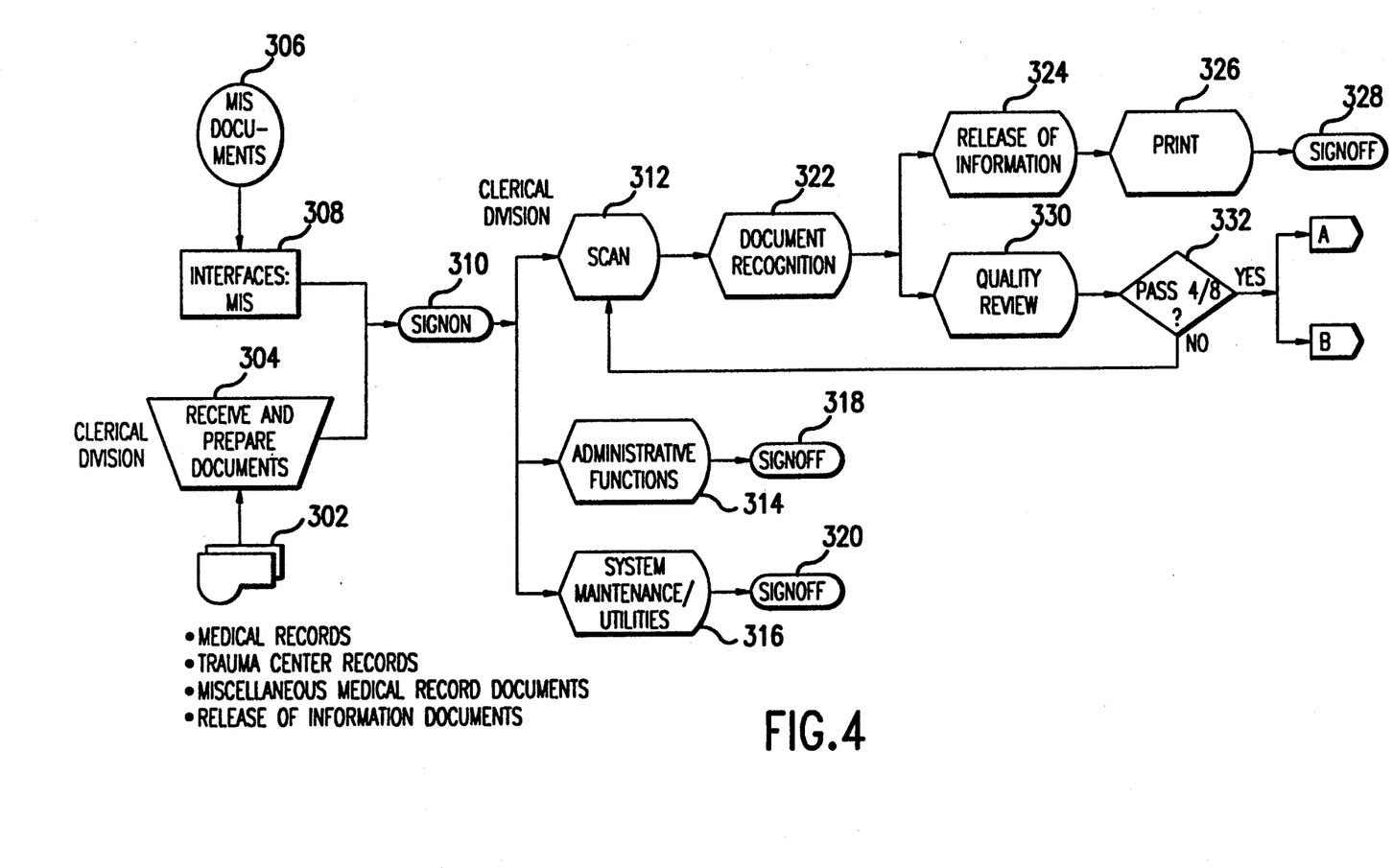
FIGS. 4–6 are flowcharts presenting an overview of the operation of a medical records imaging system utilizing a workflow server according to the present invention.
Figure 5:
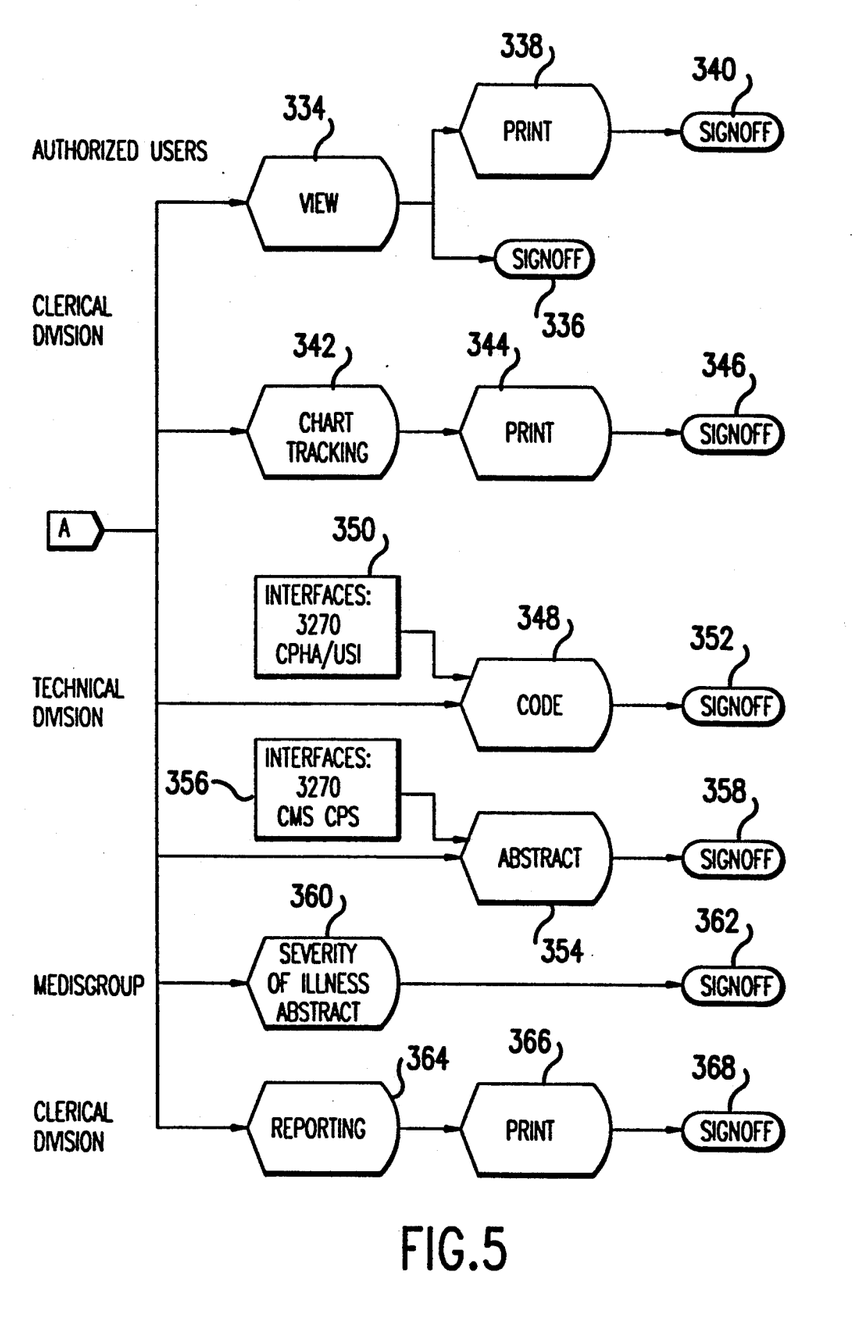
Figure 6:
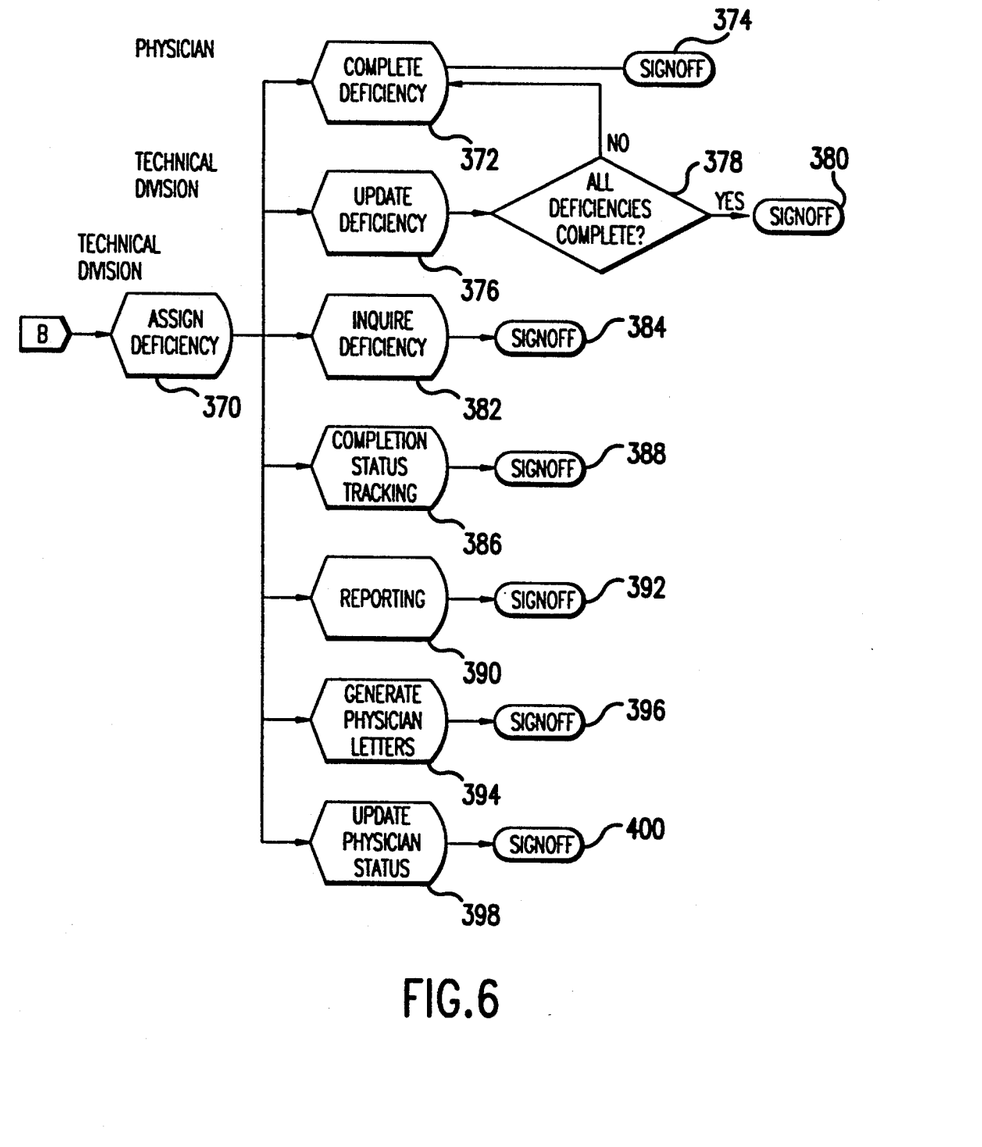

FIGS. 4–6 present an overview of the operation of a system utilizing a workflow server according to the present invention in an embodiment suitable for a hospital. As seen in FIG. 4, before a user signs on to the system at block 310, various records 302 (including medical records, trauma center records, miscellaneous medical record documents, and release of information documents) may be received and prepared for entry at block 304. Various MIS documents 306, electronically stored on one or more other computer systems, may be accessed via MIS interface 308.

At block 310, a user may sign on to the system, preferably by entering a user identification code and a password via a keyboard and CRT display of a PC workstation. If the system determines, based on previously entered information stored in the system, that a valid user identification code has been entered, and that the proper password for that user identification code has been entered, access to further features of the system is allowed.

If access is allowed, the system presents via the CRT display a menu of choices for the following system features: scan, administrative functions, and system maintenance/utilities. This and other menu choices used throughout the system may be presented horizontally across a portion of the CRT display (e.g., toward the top), in a "pull-down" or "pop-up" menu, or by other means known to those of skill in the art.

If the user selects the menu choice for scan, the system proceed to block 312, where the user may have documents entered into and stored on the system via an optical scanner. The system them proceeds to block 322, where document recognition is performed. Document recognition preferably is carried out by reading a bar code. Other methods known to those of skill in the art, such as optical character recognition (OCR), may also be used. The system then presents the user with a menu of choices for the following features: release of information and quality review. If the user selects the menu choice for release of information, the system proceeds to block 324, where the system tracks the information to be released, preferably by storing identifying data regarding the scanned document in a file for such data. The system then proceeds to block 326 where the information to be released is printed, and then the system proceeds to block 328, where the user is signed off the system. If the user selects the menu choice of quality review, the system proceeds to block 330, where tests are performed to determine whether the optical character recognition was performed successfully and whether the scan quality of the scanned document is acceptable. The system then proceeds to block 332. If the scanned document does not pass the quality review test, the system returns to block 312 and the user may attempt to scan the document again; if the scanned document passes quality review, the system proceeds, as will be discussed below.

If, following sign on at block 310, the user selects the menu choice for administrative functions, the system proceeds to block 314, where the user is presented with a number of choices. These may include valid user passwords; assigning and changing security authorization levels for each user identification number; adding or deleting patients from workqueues; updating patient data; adding or deleting record status information; and other functions dealing with administration of the system. The system then proceeds to block 318, where the user is signed off the system. Another menu choice that may be presented to the user is for system maintenance/utilities, as indicated at block 316, where the user is again presented with a number of choices. These may include moving records from a magnetic storage device to an optical storage device and other functions dealing with maintenance of the system. The system then proceeds to block 320, where the user is signed off the system. Typically, however, a general user would not be given access to such maintenance functions, and block 316 would be accessible only to certain authorized users.

If, at block 332, the system determined that quality review was passed, the user is presented with a menu of choices for the following features: view, chart tracking, code, abstract, severity of illness abstract, reporting, and assign deficiency.

As shown in FIG. 5, if the user selects the menu choice for view, and if the system determines that the user is authorized to view information records stored on the system, the system proceeds to block 334. At block 334, the user may search for and display any information record. The user may search the system using, for example, a patient's name, an identifying discharge; other search criteria may also be employed. Subsets of data may also be retrieved, e.g., selected documents for a patient for a particular physician. If a displayed information record includes certain document image data, such as a graphic display of an EKG strip, the user may magnify and rotate the document image data so that a different view is displayed.

After the user has finished viewing records, the user may choose a menu choice for signing off the system, in which case the system proceeds to block 336, or the user may choose a menu choice for printing a record, in which case the system proceeds to block 338, where the record is printed, and then proceeds to block 340, where the user is signed off.

If the user selects the menu choice for chart tracking, and if the system determines that the user is authorized, the system proceeds to block 342. There the user may search for any record stored on the system and retrieve information on the number of requests for medical chart information, to whom such information was submitted, and (if appropriate) when such information was returned. The system then proceeds to block 344, where the chart tracking information is printed, and then proceeds to sign off the user at block 346.

If the user selects the menu choice for code, and if the system determines that the user is authorized, the system proceeds to block 348. There the user may search for any record stored on the system and view a predefined subset of information regarding that record. As shown at block 350, the user may also enter appropriate diagnosis and procedure codes. For example, ICD-9-CM diagnosis and procedure codes and CPT-4 codes may be entered, via emulation of a terminal (e.g., IBM 3270) connected to a mainframe or minicomputer running encoding/grouping software. Following coding, the system proceeds to sign off the user at block 352.

If the user selects the menu choice for abstract, and if the system determines that the user is authorized, the system proceeds to block 354. There the user may search for any record stored on the system and view another predefined subset of information regarding that record. As shown at block 356, the user may also enter abstract data. For example, a hospital's Case Mix System (CMS) abstract data may be entered via terminal emulation (e.g., IBM 3270) of a CMS online CSP data entry system. Following entry of abstract data, the system proceeds to block 358, where the user is signed off.

If the user selects the menu choice for severity of illness abstract, and if the system determines that the user is authorized, the system proceeds to block 360. There the user may search for any record stored on the system and view yet another predefined subset of information regarding that record. Users may compare the displayed document image to a hard copy medical record to complete forms, such as Medisgroup Abstract forms.

If the user selects the menu choice for reporting, and if the system determines that the user is authorized, the system proceeds to block 364. There the user may request one or more reports from a predefined set of reports. Such reports may include application and control reports (e.g., data on chart deficiencies, chart tracking, correspondence), productivity reports (e g., number of medical records updated by each medical records clerk), and management reports (e.g., weekly data to monitor departmental productivity against previously defined goals). After the user requests the reports, the system proceeds to block 366, where the reports are printed, and then to block 368, where the user signs off.

As shown in FIG. 6, if the user selects the menu choice for assign deficiency, and if the system determines that the user is authorized, the system proceeds to block 370. There the system allows the user to view a predefined subset of records of an encounter (an inpatient or outpatient admission) and to assign medical record deficiencies to one or more physicians by entering one or more physician identification numbers. The user may also assign a status code of "hold" to a record (to mark its place in a workqueue while processing is delayed), or a code of "pend" (to place it back in a workqueue on a pending date).

After a user completes the assign deficiency function, the system presents the user with a menu of choices for the following features: complete deficiency, update deficiency, inquire deficiency, completion status tracking, generate reports, generate physician letters, and update physician status.

If the user selects the menu choice for complete deficiency, and if the system determines that the user is authorized, the system proceeds to block 372. There the system allows the user to view only the medical record deficiencies assigned to that user during the assign deficiency function at block 370. The system allows the user to complete deficiencies in medical record documents (e.g., an admission record), sign either Diagnosis Related Group (DRG) attestations or entire medical records electronically via keyboard, mouse, or other entry, or view a subset of an encounter lacking dictation so that a physician may dictate medical record documents (e.g., discharge summaries, consultations, or operative reports). When all deficiencies are removed, the system changes the status of a chart to "complete". After the user has finished the complete deficiency function, the system proceeds to block 374 where the user signs off.

If the user selects the menu choice for update deficiency, and if the system determines that the user is authorized, the system proceeds to block 376. There the system allows the user to update information that was entered in the assign deficiency function at block 370. After the user has finished the update deficiency function, the system proceeds to block 378, where the system determines whether all deficiencies are complete for the records updated by the user. If not, the system proceeds to block 372 to allow an authorized user to complete the deficiencies; if so, the system proceeds to block 380, where the user signs off.

If the user selects the menu choice for inquire deficiency, and if the system determines that the user is authorized, the system proceeds to block 382. There the system allows the user to view the deficiency status of each incomplete medical record, the provider status for a physician (described below), and the total number of deficient medical records (incomplete and delinquent) for a physician. After the user has completed the inquire deficiency function, the user signs off at block 384.

If the user selects the menu choice for completion status tracking, and if the system determines that the user is authorized, the system proceeds to block 386. There the system, preferably through batch processing, allows the user to track a physician's provider status and record deficiency status. The provider status is with regard to medical record completion, and preferably indicates by codes one of four conditions: (1) current—no incomplete records; (2) incomplete; (3) delinquent; and (4) suspended. The system maintains for each encounter a count of the number of days a physician allows a deficiency to remain. When the number of days exceeds a predefined parameter (e.g., 30 days), the system updates the provider status and the record deficiency status to "delinquent". The codes for provider status and record deficiency status are made available to the user in the system functions for update deficiency (block 376), inquire deficiency (block 382), reporting (block 390), and generate physician letters (block 394), so that authorized users may act on such statuses when using these system functions. When the user has finished the completion status tracking function, he signs off at block 388.

If the user selects the menu choice for reporting, and if the system determines that the user is authorized, the system proceeds to block 390. There, as at block 364 the system allows the user to request a predefined set of reports to be printed either immediately or through batch processing at a later time (e.g., over night). After the user has completed the reporting function, the system proceeds to block 392, where the user signs off.

If the user selects the menu choice for generate physician letters, and if the system determines that the user is authorized, the system proceeds to block 394. There the user may request the printing of notification letters regarding deficiencies addressed to individual physicians. One or more versions of such notification letters (e.g., first and second notification) are stored on the system as document images in the chart deficiency database. Other versions of such letters may also be scanned into the system. After the user completes the generate physician letters function, the user signs off at block 396.

If the user selects the menu choice for update physician status, and if the system determines that the user is authorized, the system proceeds to block 398. There the user may change status codes for individual physicians. Such status codes may include provider status (defined above); activity status (e.g., (1) active admitting staff, (2) active non-admitting staff, (3) active resident staff, and (4) inactive staff); and availability status (e.g., (1) available, (2) vacation, (3) illness, (4) leave of absence). When the user has completed the update physician status function, the system proceeds to block 400, where the user signs off.

Figure 7:
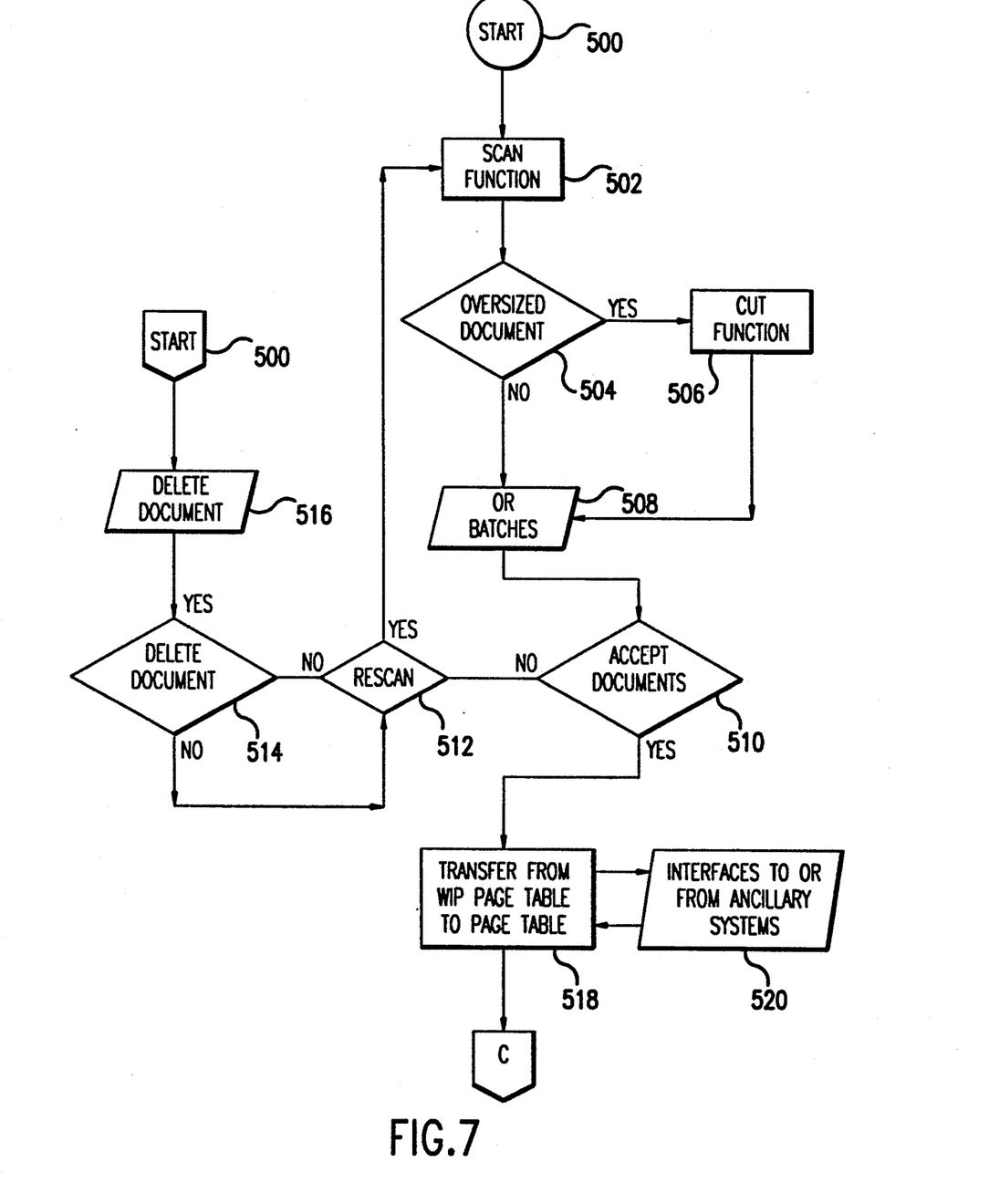
FIGS. 7–9 are flowcharts depicting operation of one embodiment of a system employing a workflow server according to the present invention.
Figure 8:
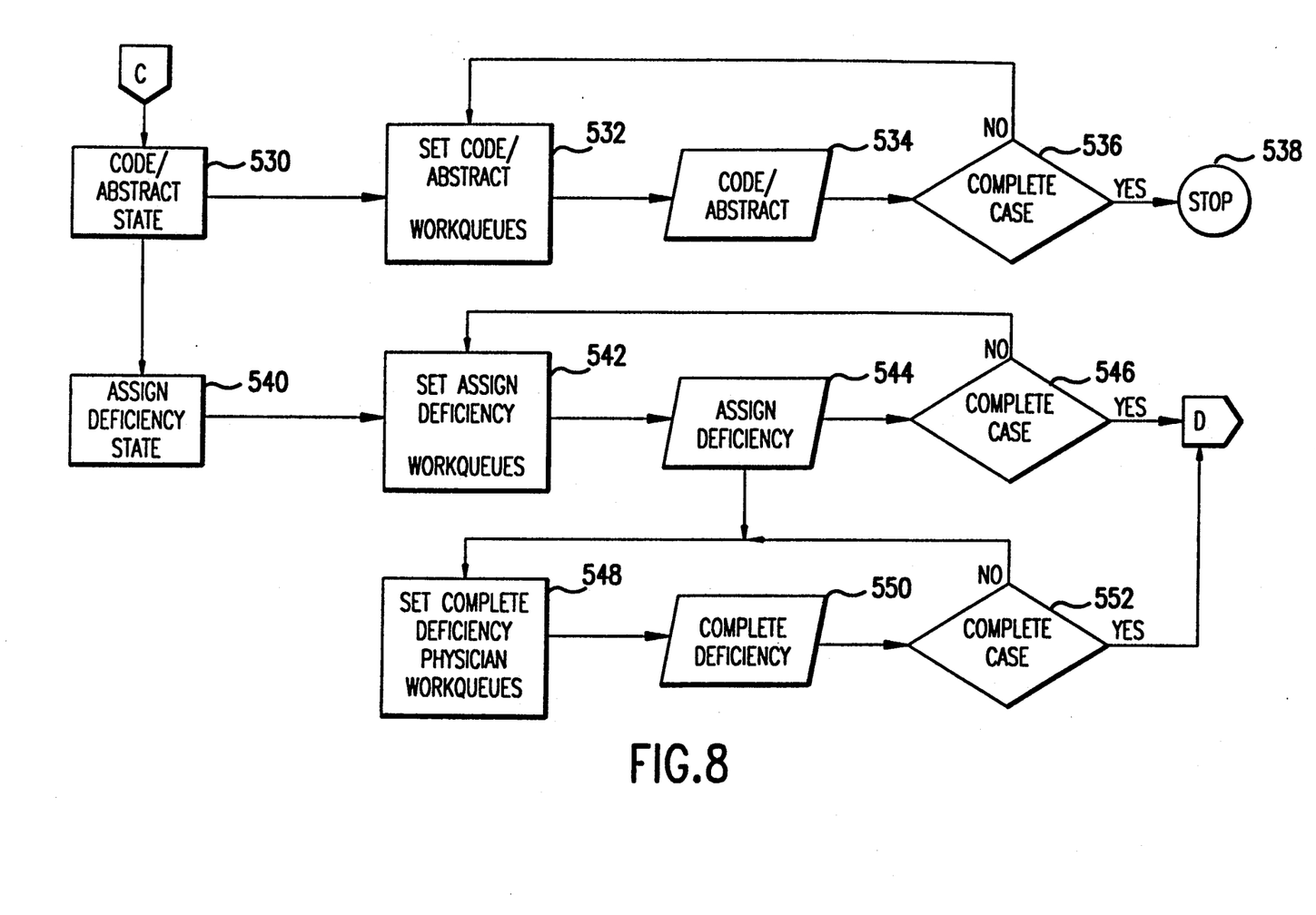
Figure 9:
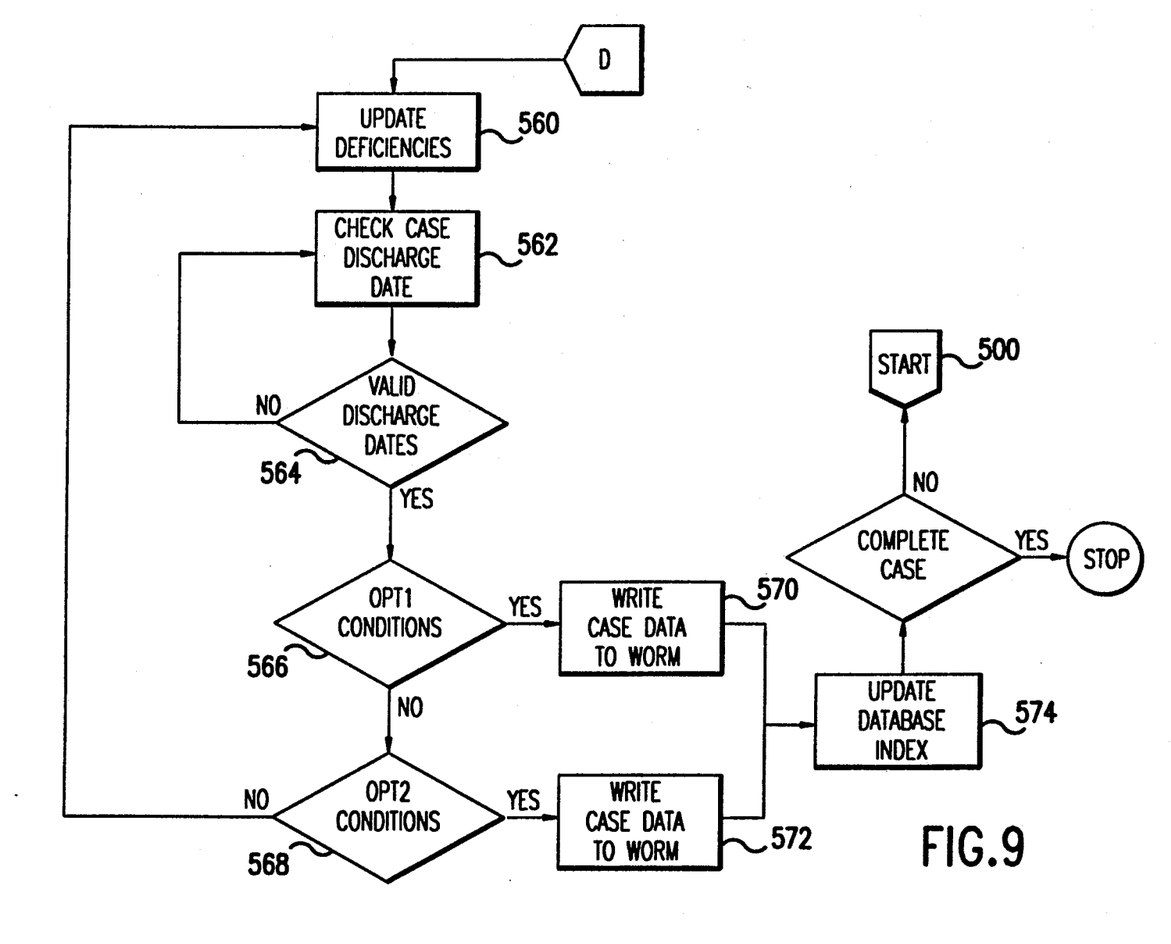

FIGS. 7-9 are flowcharts that depict the operation of a workflow server according to the present invention. The workflow server is preferably implemented on the file server as a single application program that runs in the background while other client application programs may be run.

One such client application is the scan application program, which processes the entry of medical record document data into page table 288. As shown in FIG. 7, the scan application starts at block 500 and proceeds to block 502, where the scan function is performed. By monitoring the document IDs as they are scanned at block 502, the scan application determines when all of the documents for a single batch of documents have been entered, preferably by the use of one or more identifying cover documents. After a batch of documents is scanned, the application proceeds to block 504 to determine if one or more oversized documents were scanned. If so, the application proceeds to a cut function at block 506, and then to block 508; if not, the application proceeds directly to block 508, where the quality review (QR) function is performed.

The scan application program proceeds to block 510, where an operator determines if a document will be accepted. If not, the application proceeds to block 512 so that the operator may decide whether to rescan the document. If a rescan is desired, the application returns to the scan function at block 502; if not the application proceeds to block 514. There the operator may decide whether to delete the document. If deletion is desired, the application proceeds to block 516, where the document is deleted, and then to the start of the application at block 500; if not, the application returns to block 512.

If, at block 510, the operator determines that a document will be accepted, the scan application program proceeds to block 518, where a WIP-to-page application program running on the file server transfers data from WIP page table 284 to page table 288. The file server may also transfer data received via interfaces from ancillary systems (e.g., from MIS integration 290) to page table 288. Optionally, the system may also send information to ancillary systems, as indicated at block 520.

As part of the processing at block 518, the WIP-to-page application analyzes the documents in the page table to create for each encounter subsets of records called visit cases. Each visit case contains documents related to an encounter that are to be acted upon by various application programs within the system. The workflow server maintains data regarding states that correspond to each of those application programs. Examples of this would be two states that correspond to the two application programs that implement the coding/abstracting function and the assign deficiency function. The workflow server routes each case to a workqueue within a state. If more than one resource is listed within a workqueue, a workqueue administration application then can assign each case to a resource (e.g., a hospital employee) listed. If only one resource is listed, the case is assigned to that resource. Alternatively, the workflow server may include workqueue administration functionality, such that a separate application for resource assignment would be unnecessary.

As shown in FIG. 8, the system proceeds to blocks 530 and 540, where processing of the code/abstract and the assign deficiency application programs proceed in parallel. When a visit case contains documents to be processed by the code/abstract application program, that application program sends a request to the workflow server, which routes the visit case and sets it in one of the code/abstract workqueues, as indicated at block 532. The case is then routed to an individual resource (employee) for coding/abstracting, as indicated at block 534.

When the workflow server receives a request from the system, typically via a system administrator, to load cases from the database, the workflow server performs an initial load of the database into run-time memory. Run-time memory is typically read/write random access memory (RAM). The workflow server identifies which data comprises the cases that have been defined by the system and, in response to the first and subsequent requests from the application programs, routes that data to the appropriate workqueues within the appropriate states and sorts the cases within the workqueues. Whenever modifications to the data are made, the modifications are made in memory and the application program that makes the modifications sends a request for the workflow server to write the modifications from memory to the database as stored within the system. Thus, while a data-consistent image of the database is kept in memory, the system take steps to help maintain the integrity of data within the system.

At block 536, an operator determines whether a case has been completed. If the operator decides to "hold" or "pend" the case, it is taken out of the workqueue and returned for further handling by the workflow server at block 532, where the case can be placed back in a workqueue at a later time. If the operator determines that the case has been completed, this portion of the system stops at block 538. In another embodiment, the system would define coding/abstracting cases at block 532 as subsets of each visit case for processing by the coding/abstracting application, and the subsequent actions at blocks 532, 534, and 536 would be performed on the coding/abstracting cases.

The system proceeds from block 540 when a visit case contains documents to be processed by the assign deficiency application program. At block 542 that application program creates a deficiency case and sends a request to the workflow server to route the deficiency case and set it in one of the assign deficiency workqueues. The deficiency case is then routed to an individual resource (employee) to assign the document deficiency as indicated at block 534. At block 546, an operator determines whether a case has been completed. Again, if the operator decides to "hold" Or "pend" the case, it is taken out of the workqueue and returned for further handling by the workflow server at block 542, where the case can be placed back in a workqueue at a later time.

At block 544, a document within a deficiency case may be assigned, for example, to a particular physician responsible for completing the document for a particular patient encounter. The assign deficiency application program will create another subset case of documents out of the deficiency case and send a request for the workflow server to route the new case to be set in a physician workqueue for deficiency completion, as represented at block 548. When a physician logs onto the file server via a workstation 216, the workflow server will allow that physician to deal only with cases containing documents which that physician must complete. For example, a document missing a DRG attestation may be signed via an electronic signature stored on the file server. At block 552, the physician determines whether a case has been completed. A physician may also decide to "hold" or "pend" the case; if so, it is taken out of the workqueue and returned for further handling by the workflow server at block 548, where the case can be placed back in a physician workqueue at a later time.

The selection criteria used by the workflow server to determine the number of workqueues within each state, and which cases are routed to which workqueues, are contained as parameters in a configuration file. The configuration file is processed by the workflow server when the system is started, thus allowing for run-time configuration of workqueue selection criteria.

The parameters in the configuration file implement a "code as data" approach. The parameters indicate, for example, to which workqueue a particular case is assigned by indicating which program code the system should execute when processing that case. In another embodiment, the selection criteria for assigning resources within workqueues, used either by the workflow server or a workqueue administration application, may also be specified as parameters in the configuration file. Other embodiments may set further parameters in the configuration file, such as to allow for parallel routing of cases, or synchronous or asynchronous routing of cases.

Preferably, the workflow server maintains a table on a magnetic disk to store data regarding: the states available to the system for workflow processing; the workqueues available within each state; the resources available within each workqueue; the criteria for forming cases for each state; the criteria for routing cases to each workqueue; and the criteria for assigning cases to each resource.

The workflow server thus allows for automating and prioritizing the workflow of assigning cases to resources at run time with whatever sophistication a hospital requires. Based on an individual hospital's needs, several workqueues may be established for each state, and rules regarding the resources may be established for each workqueue. For example, if a hospital employs four persons to handle coding/abstracting, it may decide that two particular employees should handle that task for in-patients and the other two should work on out-patients. The workflow server may be configured to provide two workqueues in the coding/abstracting state, one for in-patients and one for out-patients.

Within each of those two-employee categories, the hospital may determine that it wants one employee to work on coding/abstracting of Medicaid documents, and the other to work on Medicare documents. A workqueue administration application (or the workflow server provided with the same functionality) can assign a particular code/abstract case within a particular workqueue to a particular resource. When, for example, the hospital employee charged with coding/abstracting in-patient Medicaid documents logs onto the file server via a workstation 214, the workflow server will allow that employee to deal only with cases containing in-patient Medicaid documents.

Alternatively, four separate workqueues could be set up for coding/abstracting of in-patient Medicaid documents, in-patient Medicare documents, out-patient Medicaid documents, and out-patient Medicare documents, with a single resource (employee) assigned to each workqueue.

As shown in FIG. 9, if a visit case is indicated to be completed at blocks 546 or 552, processing proceeds to block 560, where page table 288 is updated to indicate what deficiencies have been completed. As indicated at block 562, the discharge date for a case is checked. If, at block 564, a valid discharge date is not indicated, processing returns to block 562. If a valid discharge date is indicated, the system determines if certain user defined conditions (OPT1) have been met, at block 566; if they have not been met, the system determines whether certain other conditions (OPT2) have been met, at block 568. If the OPT1 or OPT2 conditions have been met, processing continues to blocks 570 and 572, respectively, where the case data is written to a write-once, read-many (WORM) optical disk. The system then proceeds to block 574, where the database index of page table 288 is updated, and then to block 576. There, the system determines whether the case is incomplete. If so, the system returns to the start of the scan function at block 500; if not, this portion of the system stops at block 578.

While the system, as described, preferably includes two application program states—coding/abstracting and assign deficiencies—other embodiments may include further application program states. The may process visit cases or other subsets of visit cases which would be defined by the other application program states.

A workflow server according to the present invention also preferably provides the capability for an operator to access the various workqueues via a workstation in order to override the case-to-resource assignments previously made by the workqueue administration application. For example, if a hospital employee is absent on a particular day, an administrator can transfer cases from that employee's workqueue to another employee's workqueue.

What is claimed is:

1. A computer system for storing and tracking medical information records comprising:
   means for storing data in a run-time memory;
   means for storing data regarding the medical information records in a relational database;
   means for loading the data regarding the medical information records into the run-time memory;
   means for running one or more application programs, each of which performs one or more operations on the data regarding the medical information records;
   means for identifying when data constituting a predefined set of data has been added to the database;
   means for forming one or more first subsets of said predefined set of data, each subset being formed according to predefined first subset criteria;
   means for forming one or more second subsets of each of said one or more first subsets, each second subset being formed according to predefined second subset criteria for a specific application program;
   workqueue routing means, responsive to a request from one of the application programs, for routing each first subset, according to predefined workqueue routing criteria, to a workqueue for one of the application programs, and for routing each second subset, according to predefined workqueue routing criteria, to a workqueue for the application program whose predefined second subset criteria were used to form the second subset;
   resource assigning means for assigning each first subset and second subset, according to predefined resource assigning criteria, to a resource for one workqueue; and
   means for allowing a user identified to the system as a particular resource running a particular application program access only to those first subsets or second subsets assigned to that particular resource for that resource's associated workqueue for the particular application program that is running.

2. A computer system as claimed in claim 1 further comprising means for storing configuration data regarding the application programs, the workqueues for each application program, the resources for each workqueue, the predefined first and second subset criteria, the predefined workqueue routing criteria, and the predefined resource assigning criteria.

3. A computer system as claimed in claim 2 wherein said means for storing configuration data comprises a run-time configuration file.

4. A computer system for storing and tracking medical information records comprising:
   means for storing data regarding the medical information records in a relational database;
   means for running one or more application programs, each of which performs one or more operations on data in said database;
   means for identifying when data constituting a predefined set of data has been added to the database;
   means for forming one or more subsets of said predefined set of data, each subset being formed according to predefined subset criteria;
   workqueue routing means for routing each subset, according to predefined workqueue routing criteria, to a workqueue for one of the application programs;
   resource assigning means for assigning each subset, according to predefined resource assigning criteria, to a resource for one workqueue; and
   means for allowing a user identified to the system as a particular resource running a particular application program access only to those subsets assigned to that particular resource for that resource's associated workqueue for the particular application program that is running.

5. A computer system as claimed in claim 4 further comprising means for storing configuration data regarding the application programs, the workqueues for each application program, the resources for each workqueue, the predefined subset criteria, the predefined workqueue routing criteria, and the predefined resource assigning criteria.

6. A computer system as claimed in claim 5 wherein said means for storing configuration data comprises a run-time configuration file.

7. A method for storing and tracking medical information records on a computer system comprising the steps of:
   storing data regarding the medical information records in a relational database;
   identifying when data constituting a predefined set of data has been added to the database;
   loading the data regarding the medical information records into a run-time memory in response to a request to load the data from the database;
   forming one or more first subsets of said predefined set of data, each subset being formed according to predefined first subset criteria;
   forming one or more second subsets of said first one or more subsets, each second subset being formed according to predefined second subset criteria for a specific one of one or more application programs that can run on the system, each of which performs one or more operations on data in said database;
   routing each first subset in response to a request from one of the application programs, according to predefined workqueue routing criteria, to a workqueue for one of the application programs, and routing each second subset, according to predefined workqueue routing criteria, to a workqueue for the application program whose predefined second subset criteria were used to form the second subset; and
   assigning each first subset and second subset, according to predefined resource assigning criteria, to a resource for one workqueue,
   whereby a user identified to the particular resource running a particular application program is allowed access only to those first subsets or second subsets assigned to that particular resource for that resource's associated workqueue for the particular application program that is running.

8. A method as claimed in claim 7 further comprising the step of storing on a storage medium configuration data regarding the application programs, the workqueues for each application program, the resources for each workqueue, the predefined subset criteria, the predefined workqueue routing criteria, and the predefined resource assigning criteria.

9. A computer system as claimed in claim 8 wherein said step of storing configuration data comprises storing the configuration data in a run-time configuration file.

10. A method for storing and tracking medical information records on a computer system comprising the steps of:
    storing data regarding the medical information records in a relational database;
    identifying when data constituting a predefined set of data has been added to the database;
    forming one or more subsets of said predefined set of data, each subset being formed according to predefined subset criteria;
    routing each subset, according to predefined workqueue routing criteria, to a workqueue for one of the application programs; and
    assigning each subset, according to predefined resource assigning criteria, to a resource for one workqueue,
    whereby a user identified to the system as a particular resource running a particular application program is allowed access only to those subsets assigned to that particular resource for that resource's associated workqueue for the particular application program that is running.

11. A method as claimed in claim 10 further comprising the step of storing on a storage medium configuration data regarding the application programs, the workqueues for each application program, the resources for each workqueue, the predefined subset criteria, the predefined workqueue routing criteria, and the predefined resource assigning criteria.

12. A method as claimed in claim 11 wherein said step of storing configuration data comprises storing the configuration data in a run-time configuration file.

* * * * *